United States Patent [19]

Chang

[11] Patent Number: 5,204,451

[45] Date of Patent: Apr. 20, 1993

[54] ACTIVATING HYDROXYL GROUPS OF POLYMERIC CARRIERS USING 4-FLUOROBENZENESULFONYL CHLORIDE FOR BINDING BIOLOGICALLY ACTIVE LIGANDS

[75] Inventor: Yu-An Chang, Costa Mesa, Calif.

[73] Assignee: Baxter International Inc., Deerfield, Ill.

[21] Appl. No.: 567,481

[22] Filed: Aug. 13, 1990

[51] Int. Cl.$^5$ ............... C07K 17/00; C12N 11/12; C12N 11/10; G01N 33/544

[52] U.S. Cl. ................... 530/413; 435/178; 435/179; 435/180; 435/803; 436/529; 436/530; 436/531; 436/824; 530/813; 530/814; 530/815

[58] Field of Search ............ 435/177, 178, 179, 180, 435/181, 803; 436/530, 529, 531, 532, 824; 530/813, 814, 815, 816, 413

[56] References Cited

U.S. PATENT DOCUMENTS

| | | | |
|---|---|---|---|
| 3,843,324 | 10/1974 | Edelman et al. | 23/230 B |
| 4,230,685 | 10/1980 | Senyei et al. | 436/526 |
| 4,252,653 | 2/1981 | Beck et al. | 210/321.3 |
| 4,415,665 | 11/1983 | Mosbach et al. | 435/179 |
| 4,438,245 | 3/1984 | Satomura | 526/288 X |
| 4,554,088 | 11/1985 | Whitehead et al. | 436/526 X |
| 4,582,875 | 4/1986 | Ngo | 425/54.11 |
| 4,628,037 | 12/1986 | Chagnon et al. | 436/526 |
| 4,648,974 | 3/1987 | Rosskopf et al. | 210/651 |

OTHER PUBLICATIONS

"Removal of Neuroblastoma Cells From Bone Marrow with Monoclonal Antibodies Conjugated to Magnetic Microspheres" J. Treleaven, J. Ugelstad, T. Philips, F. M. Gibson, A. Rembaum, G. D. Caines and J. T. Hemshead, *The Lancet*, Jan. 14, 1898, pp. 70-73.

"Immunomagnetic removal of B-lymphoma cells from human bone marrow; a procedure for clinical use", G. Kvalheim, O. Sorensen, O. Fodstad, S. Eunderud, S. Kiesel, B. Dorken, K. Nustad, E. Jakbosen, J. Ugelstad, A. Pihl, *Bone Marrow Transplantation* (1988) vol. 3, pp. 31-41.

*Primary Examiner*—David M. Naff
*Attorney, Agent, or Firm*—Michael C. Schiffer; Janice Guthrie

[57] ABSTRACT

The invention relates to a method of binding biologically active organic ligands to hydroxyl groups of polymeric carriers. The method involves bringing 4-fluorobenzenesulfonyl Chloride into reactive contact with the hydroxyl groups of polymeric carriers in such a manner to form sulfonate groups in place of the hydroxyl groups. The ligand is then brought into reactive contact with the hydroxyl groups of polymeric carriers to replace the sulfonate groups reacted with the organic ligand. The polymeric carrier containing the bound ligand can be used to isolate a biologically active material from a heterogeneous solution.

13 Claims, No Drawings

ACTIVATING HYDROXYL GROUPS OF POLYMERIC CARRIERS USING 4-FLUOROBENZENESULFONYL CHLORIDE FOR BINDING BIOLOGICALLY ACTIVE LIGANDS

BACKGROUND OF THE INVENTION

The present invention relates to the use of 4-fluorobenzenesulfonyl Chloride for activating hydroxyl groups of polymeric carriers forming biospecific affinity supports. More specifically, the present invention is a method of forming biospecific affinity supports involving the activation of the hydroxyl groups of polymeric carriers with 4-fluorobenzenesulfonyl Chloride for subsequent reaction with biologically active organic ligand having amino or sulfohydryl groups, the biospecific affinity support is useful in a separation procedure.

Recent advances in separation technology allow isolating a specific target population, e.g. cells, proteins, or antibodies, from a heterogeneous solution without the need of tedious and extensive chemical separation techniques. These recent advances involve the use of biospecific affinity supports. Biospecific affinity supports are typically formed from hydroxyl bearing polymeric carriers, in the form of columns, gels or polymeric beads, to which a biologically active organic ligand is chemically bonded. The biologically active organic ligand has selective affinity for bonding to the desired target population, i.e. proteins, enzymes, antibodies and antigens, from solutions.

Biologically active organic ligand are compounds that selectively bind to the desired biologically active target population. One specific example of a biologically active target population is an antigen or enzyme, with the biologically active organic ligand being an antibody selective for the biologically active target population.

Biospecific affinity supports are used in various types of separation techniques. For example, biospecific affinity supports are used in immunologic methods and in affinity chromatography wherein antibodies or antigens are bonded to water insoluble polymeric carriers to function as the biologically active organic ligand.

Various workers have also suggested capturing specific target populations by using filters bearing biologically active organic ligand. These techniques may use filters prepared from fibers, e.g. disclosed in U.S. Pat. No. 3,843,324, issued on Oct. 22, 1974; or columns, e.g. disclosed in U.S. Pat. No. 4,252,653, issued on Feb. 24, 1981; or filter candles, e.g. disclosed in U.S. Pat. No. 4,648,974, issued Mar. 10, 1987.

Another recently developed technique for isolating target populations, i.e. antibodies, selected proteins and cells, from a physiological fluid utilizes paramagnetic beads or particles coated with an biologically active organic ligand selective for the desired target population. Examples of such particles or beads are disclosed in U.S. Pat. Nos. 4,230,685, issued Oct. 28, 1980; 4,554,088, issued Nov. 19, 1985; and 4,628,037, issued Dec. 9, 1986. The use of such particles in the separation of cells is taught in publications, "Removal of Neuroblastoma Cells From Bone Marrow with Monoclonal Antibodies Conjugated to Magnetic Microspheres", by J. G. Treleaven, J. Ugelstad, T. Philips, F. M. Gibson, A. Rembaum, G. D. Caines and J. T. Kemshead, *The Lancet*, Jan. 14, 1984, pages 70–73, and "Immunomagnetic removal of B-lymphoma cells from human bone marrow: a procedure for clinical use", by G. Kvalheim, O. Sorensen, O. Fodstad, S. Funderud, S. Kiesel, B. Dorken, K. Nustad, E. Jakobsen, J. Ugelstad and A. Pihl, *Bone Marrow Transplantation*, (1988), volume 3, pages 31–41.

There are various known methods for chemically coupling biologically active ligand to hydroxyl bearing polymeric substrates. Some workers demonstrated the use of cyanogen bromide (CNBr) as a compound for activating the hydroxyl groups of hydroxyl bearing polymeric substrates. The biologically active organic ligand is then reacted with the activated hydroxyl groups, see Scouten, et al "Methods in Enzymology 135, 79 (1987). There are disadvantages in using cyanogen bromide for activating hydroxyl groups of polymeric carriers. The chemical linkages formed between the hydroxyl bearing polymeric substrates and biologically active organic ligand are known to be liable. The activated polymeric carrier is not stable, and cyanogen bromide is a noxious, lachrymator and poisonous chemical which requires special handling procedures.

Other workers suggest the use of 2-Fluoro-1-methyl-pyridinium toluene-4-sulfonate (FMP), see U.S. Pat. No. 4,582,875, issued to Ngo on Apr. 15, 1986. A disadvantage associated with FMP as an activating agent is the formation of a positively charged quaternary amine group on the chemically activated polymeric carrier. The presence of the positively charged group makes displacement of this group by similarly charged ligand more difficult and less efficient.

Other workers have activated the hydroxyl groups of hydroxyl bearing polymeric substrates using sulfonyl halogenids (sulfonyl halides), see U.S. Pat. No. 4,415,665, issued to Mosbach et al on Nov. 15, 1983. This patent describes a method utilizing a sulfonyl halogenoid having the formula:

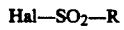

Hal—SO$_2$—R wherein R is any organic group suitable for the sulfonyl chloride. Examples of suitable R groups include p-tolyl, p-nitrolphenyl, trifluoroethyl, trifluoromethyl or methyl. While Mosbach et al discloses the use of sulfonyl halogenids in general, the patentees only utilize two specific halogenids, p-toluenesulfonyl and 2,2,2-trifluoroethanesulfonyl chloride. There are distinct disadvantages with each of these halogenids or halides. P-toluenesulfonyl chloride has been demonstrated as being primarily reactive with the secondary, but not the primary hydroxyl groups of the hydroxyl bearing polymeric substrate. This limits the degree of activation obtainable with p-toluenesulfonyl, which limits the amount of ligand that can be attached to the carrier. It has also been demonstrated that reaction between the p-toluenesulfonate groups and the biologically active organic ligand often requires 16 to 24 hours incubation under conditions of Ph 8.0 or higher, which may be damaging to sensitive biologically active organic ligand, such as enzymes or antibodies. Damage to these ligand decreases the usefulness of the ligand coupled carrier.

2,2,2-trifluoroethanesulfonyl chloride (tresyl chloride) is toxic, highly reactive and volatile, making use of this material for the activation of the hydroxyl groups of polymeric carriers difficult. Tresyl chloride is typically used in well-ventilated environments. The volatility and high reactivity of tresyl chloride requires that the activation be performed under water-free solvent; dried solvents, rather than commercially available solvents. The use of commercially available solvents lowers the yield of the activation reaction. Unlike the other activation methods, the introduction of the tresyl ester, which results from the reaction of tresyl chloride and the hydroxyl groups, can not be followed with UV spectroscopy. Tresyl chloride is also more expensive than other halides.

The present invention is an improvement of the method disclosed in the Mosbach patent. The applicants' have found that a specific sulfonyl halogenoid, 4-fluorobenzenesulfonyl Chloride, provides unexpected benefits over sulfonyl halogenids in general, and p-toluenesulfonyl and 2,2,2-trifluoroethanesulfonyl chloride in particular.

SUMMARY OF THE INVENTION

The method of the invention provides improvements over the above described techniques for binding biologically active organic ligand to hydroxyl groups of polymeric carriers. The method of the invention first involves activating the hydroxyl groups of a hydroxyl bearing polymeric substrate with 4-fluorobenzenesulfonyl Chloride. The substrate is then contacted with the desired biologically active organic ligand which is selective for the desired biologically active target population. The second step of contacting the substrate with the ligand may either be performed directly after the activation of the hydroxyl groups, or the hydroxyl bearing polymeric substrate may be stored in wet or dry form.

DESCRIPTION OF THE PREFERRED EMBODIMENTS

The present invention is an improvement over the method taught in Mosbach et al. More specifically, the present invention is directed at activating hydroxyl groups of a polymeric substrate with a specific halogenoid, 4-fluorobenzenesulfonyl Chloride. 4-fluorobenzenesulfonyl Chloride provides unexpected benefits over sulfonyl halogenids in general and the sulfonyl halogenids recited in Mosbach et al, and in particular p-toluenesulfonyl chloride and 2,2,2-trifluoroethanesulfonyl chloride.

Specifically, 4-fluorobenzenesulfonyl Chloride is not as toxic nor does it possess the volatility of 2,2,2-trifluoroethanesulfonyl chloride. Further, 4-fluorobenzenesulfonyl Chloride is believed to be more reactive with primary hydroxyl groups than p-toluenesulfonyl chloride.

The physical chemistry of 4-fluorobenzenesulfonyl Chloride enhances its replacement by the ligand on the substrate. The replacement of the ligand for the 4-fluorobenzenesulfonyl Chloride is enhanced as a direct result of the para fluoro substitution on the aromatic ring of the 4-fluorobenzene sulfonate. This para fluoro substitution imparts an electron withdrawing effect making the 4-fluorobenzene sulfonate an excellent leaving group. Substitution of ligand for the 4-fluorobenzenesulfonyl Chloride group on the substrate is completed in 6 hours instead of 16 or more hours required for the p-toluenesulfonyl chloride. Processing time is thus reduced while biological activity is conserved.

The polymeric carriers useful for practicing the method of the invention include a carrier substrate formed from a suitable polymeric material. The polymeric material should have sufficient hydroxyl groups for attachment by the biologically active organic ligand. Suitable polymeric materials include water-insoluble or water-soluble polymeric substances, and specifically polystyrene, copolymers of polystyrene and other polymers, polysaccharides such as cellulose or sepharose, or cross-linked agarose. The carrier substrate may be in the form of microspheres, beads, fibers, rods or other suitable shape.

Biologically active organic ligand include antibodies, antigens, enzymes, and similar protein compounds and complexes. The ligand are selectively active with other protein compounds or complexes which comprise the target population. For example, an antigen may form the ligand which is selectively active with an specific antibody target population contained in a heterogenous solution.

The reaction scheme of the method of the invention generally involves two steps: (1) Activation of the hydroxyl groups with the 4-fluorobenzenesulfonyl Chloride; and (2) substitution or replacement of the formed sulfonate group with the desired ligand.

The activation of the hydroxyl groups involves bringing the 4-fluorobenzenesulfonyl Chloride into reactive contact with the polymeric carrier. The reaction between the 4-fluorobenzenesulfonyl Chloride and the hydroxyl groups of the polymeric carrier is illustrated as follows:

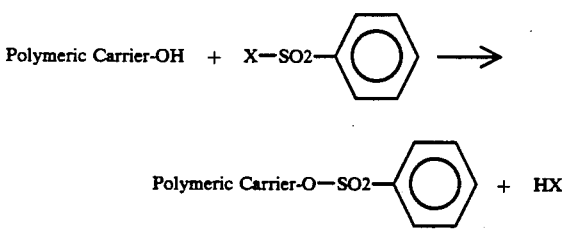

wherein X is a halogen, e.g. chlorine, bromine or iodine, but preferably chlorine.

The 4-fluorobenzenesulfonyl chloride reacts rapidly with primary or secondary hydroxyl groups, usually in less than 45 min under ambient temperature and pressure, to form 4-fluorobenzenesulfonate groups. This reactive derivative can be used immediately or can be preserved either by freeze-drying or stored at 4° C. at pH 5 aqueous solution for future use.

The activation of the hydroxyl groups may be performed in the presence of a small quantity of tertiary amine such as triethyl amine, dimethyl aminopyridine (DMAP) or pyridine in a dry polar organic solvent such as acetonitrile, acetone or tetrahydrofuran.

The unreacted 4-fluorobenzenesulfonyl chloride, triethyl amine, pyridine and DMAP are removed by washing with organic solvent (e.g. acetonitrile) followed by deionized water The substitution reaction involves bringing the desired biologically active organic ligand into reactive contact with the 4-fluorobenzenesulfonate groups of polymeric carrier. The 4-fluorobenzenesulfonate groups react readily with any group capable of displacing the 4-fluorobenzenesulfonate groups from the polymeric carrier, preferably amino or sulfhydryl groups. The substitution of the 4-fluorobenzenesulfonate groups by the ligand bearing amino or sulfhydryl groups is illustrated as follows:

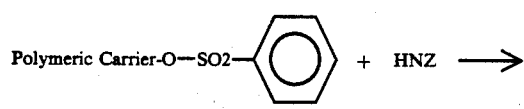

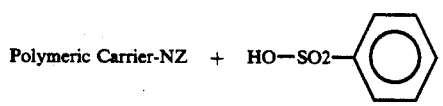

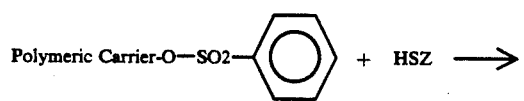

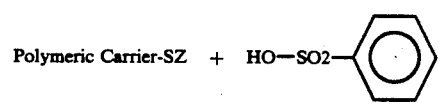

wherein Z represents the ligand backbone molecule.

The substitution reaction can be carried out under various conditions as to temperature, ph and solvents. The substitution reaction may be performed in aqueous, inert or other suitable mediums. While the reaction conditions, i.e. ph and temperature are not critical for either step of the invention, such conditions should be selectively chosen for the specific components being used, i.e. the polymeric carrier and the ligand.

The unreacted 4- Fluorobenzenesulfonate groups can be easily removed by incubation with 0.05M ph 8 Tris buffer at ambient temperature overnight.

The following examples will help to make the invention demonstrate the effectiveness of using 4-fluorobenzenesulfonyl Chloride in binding selective ligand to different substrates.

EXAMPLE 1

Activation of cross-linked agarose beads with 4-fluorobenzenesulfonyl chloride (1)

2.04 g of Sepharose beads ® (agrose beads manufactured by the Sigma Chemical Co., St. Louis, Mo. Stock Number CL-4B-200) were filtered and washed once with 15 ml deionized water and then with 15 ml acetontrile three times to remove water, then 7 ml acetonitrile/Demethlyamino pyridine (DMAP)/Et$_3$N (9 ml/100 mg/1 ml) solution was added to the beads; 4 fluorobenzenesulfonyl chloride 2.03 g was added to the test tube and the capped tube was rotated at ambient temperature for one hour (2)

The reagents were removed by filtration, then the beads were washed with acetonitrile 7 ml and deionized water 7 ml (3)

10 ml deionized water and 3 drops of 1N HCl were added to the beads to decrease the solution pH to 5 and then the chemically activated beads were sealed in the test tube with paraffin and stored at 4° C. in a refrigerator for future coupling of biological

EXAMPLE 2

Activation of cellulose fiber with 4-fluorobenzenesulfonyl chloride (1)

200 mg cellulose fiber (manufactured by the Sigma Chemical Co., St. Louis, Mo., Stock Number C-6288) was washed three times with 2 ml acetonitrile and then 4 ml of a solution of aceontrile/DMAP/Et$_3$N (9 ml/100 mg/1 ml) was added to the sample (2)

4-fluorobenzenesulfonyl chloride (200 mg) was added to the test tube (3)

The tube was rotated at ambient temperature for 2 hours (4)

The reagents were removed by filtration and the fiber was washed with 2 ml of deionized water three times.

(5)

The fiber sample was then stored at 4° C. in a refrigerator with or without freeze-drying for future coupling to biological.

EXAMPLE 3

Activation of cellulose rod with 4-fluorobenzenesulfonyl chloride (1)

A solution of 10 ml of acetonitrile/DMAP/Et$_3$N (9 ml/100 mg/1 ml) was added to 120 mg of cellulose rod(NB # 1355-62-25) and then 4-fluorobenzenesulfonyl chloride (400 mg) was added to the test tube and the tube was rotated at ambient temperature for 1½ hours (2)

The reagents were removed by filtration and the rod was washed with acetonitrile (2 ml) three times and deionized water (2 ml) three times (3)

The sample was freeze-dried overnight and then sealed by paraffin and stored at 4° C. in a refrigerator for future coupling of biological.

EXAMPLE 4

Activation of biocompatible maleated cellulose rod with 4-fluorobenzenesulfonyl chloride (1)

A solution of 2 ml of acetonitrile/DMAP/Et$_3$N (9 ml/100 mg/1 ml) was added to the maleated cellulose rod (32.4 mg) then 4-fluorobenzenesulfonyl chloride (97 mg) was added to the solution. The tube was rotated at ambient temperature for one hour.

(2)

The reagents were removed by filtration then the cellulose rod was washed with acetonitrile (2 ml) three times and deionized water (2 ml) three times.

(3)

The sample was then freeze-dried and stored at 4° C. or used directly for coupling of biological.

EXAMPLE 5

Activation of polystyrene paramagnetic beads with 4-fluorobenzenesulfonyl chloride (1)

5 ml of DYNABEADS M450 (an uncoated polystrene paramagnetic beads manufactured by the Dynal A. S., Norway Product No. 14001/14002) were washed with deionized water (3 ml) three times followed by acetonitrile (3 ml) three times. The beads were then resuspended in 6 ml acetonitrile, 0.08 ml pyridine, 160 mg DMAP and then 4-fluorobenzenesulfonyl chloride (600 mg) was added to the solution.

(2)

The test tube was rotated at ambient temperature for six hours and then the beads were washed with acetonitrile (3 ml) four times followed by deionized water (3 ml) four times (3)

The beads were then freeze-dried and stored at 4° C. or used directly for coupling to biological.

The following examples demonstrate the substitution of 4-fluorobenzenesulfonate groups by various biologically active organic ligand on various hydroxyl groups of polymeric carriers. The examples further provide illustration of the use of the substrates bearing the ligand for isolation of a target population.

EXAMPLE 6

Coupling of avidin to activated magnetic polystyrene beads and the use of the substrate for isolating a specific cell.

(1)

16 mg of the DYNBEADS® M450 prepared in Example 5 were resuspended in 1 ml Borate buffer, pH 8.9.

(2)

500 ug egg white avidin was added to the beads and the sample rotated overnight at ambient temperature.

(3)

Goat anti-mouse polyclonal antibody (obtained from Jackson Immunoresearch Laboratories, Inc., Code No. 115-005-071) was biotinylated following the biotinylating reagent supplier's directions and then buffer exchanged to a phosphate buffered saline solution.

(4)

The biotinylated antibody was incubated with the avidin coated beads overnight at ambient temperature and then washed three times with phosphate buffered saline and resuspended in the same buffer Cell Depletion (1)

Aliquots containing $2 \times 10^7$ beads were pipetted into $12 \times 75$ mm glass test tubes and washed with 0.5 to 1.0 ml DPBS, using a magnet for collection of the beads (2)

Any antibody non-specifically bound to the beads were removed by incubating the beads with 0.5 to 1.0 ml DPBS containing 10% Fetal Bovine Serum (FBS) for 30 min at ambient temperature, and then washing twice with 2 ml DPBS containing 2% FBS and centrifuging at a high speed for 1 minute (the centrifuge used for all experiments was one purchased from Serofuge).

(3)

The centrifuge pellet was divided into two alquots and selectively incubated with one of two commercially available mouse monoclonal antibodies (the mouse antibodies recognized either the CD3 or the CD4 antigen site on human lymphocytes) for 30 min at 4° C. with occasional mixing.

(4)

All bead samples were then washed three times with 2 ml DPBS/2% FBS and the final pellets resuspended in 400 µl of DPBS/2% FBS and refrigerated at 4° C. until the addition of human lymphocytes (5)

Human lymphocytes were isolated from peripheral blood using standard ficoll-hypaque separation techniques. Following the addition of $2 \times 10^6$ cells to each tube in a final volume of 500 µl, the tubes were capped and rotated for 30 min at 4° C.

(6)

The beads with attached cells were then collected using the magnets and the supernatant transferred to $12 \times 75$ mm polypropylene test tubes. A solution of 2 ml of DPBS containing 2% FBS and 0.02% sodium azide was added to each tube and the tubes were spun at high speed for 1 min. on the centrifuge and the supernatant decanted and the tube rims blotted.

(7)

Analysis of pre and post treatment cell samples were performed using standard cytofluorograph techniques with fluorescent labeled goat antimouse antibody to determine the percent of either CD3 or CD4 remaining in solution after the depleting the cell population with the addition of the beads.

(8)

The percentages of the two lymphocyte subsets before and after specific cell depletion are shown below:

| Predepletion:  | CD4 | 37.4%  |
|----------------|-----|--------|
|                | CD3 | 58.0%  |
| Postdepletion: | CD4 | 0.00%  |
|                | CD3 | 0.69%  |

In each case the specific binding and biological function of the goat antimouse antibody on the beads was apparent through test and the control samples.

EXAMPLE 7

Coupling of Catalase enzyme to activated cellulose fiber (1)

To 50 mg of the 4-fluorobenzenesulfonyl chloride activated cellulose fiber prepared in Example 2 was added 1 ml borate buffer (0.05M, pH 9) and 0.1 ml gmg catalase enzyme. The fiber was then rotated at ambient temperature for 1 hour.

(2)

The fiber was filtered and washed with Tris/0.1%. Tween 20 (purchased from Sigma Chemicals Company, Inc. St. Louis, Mo. 0.05M, pH 8, 2 ml) three times and 2 ml Tris/Tween 20 was added to the fiber rotated at ambient temperature for 1.5 hours to remove the non-specific bound catalase. The fiber was then washed with 0.05M phosphate buffer (pH 7, 2 ml) three times and filtered

Measurement of Enzyme Activity (3)

10 mg of the washed and filtered fiber was added to 4 ml phosphate buffer (0.05M, pH 7) and 100 μl this suspension was added to 30 ml of a hydrogen peroxide substrate solution (30% hydrogen peroxide solution diluted by 0.05M, pH 7 phosphate buffer until achieving about 5.3 at $A_{240nm}$ using spectraphotometer and standardized concentration curves). The suspension was stirred at ambient temperature and 1.5 ml aliquots were withdrawn and checked for decreasing $A_{240nm}$ at various time intervals.

(4)

Calculate the activity unit by the following formula:
Activity unit=$(3.45/X) \times 10$ (dilution factor)
$X$ =Time (min) required for $A_{240nm}$ decreased from 0.45 to 0.40
average activity unit for the cellulose fiber was 9.5 units/mg fiber
average amount of catalase bound on the fiber was 0.2 ug/mg fiber
Again, a spectraphotometer was used to measure activity at $A_{240nm}$ for the sample which was compared against a standardization curve for known concentrations.

EXAMPLE 8

Coupling of Bovine Liver Catalase Enzyme to activated Sepharose Beads (1)

10 mg of the 4-fluorobenzenesulfonyl chloride activated Sepharose ® beads prepared in Example 1 was added 2 ml borate buffer (0.05M, pH 9) and 9 mg bovine liver catalase enzyme. The sample was then rotated at ambient temperature for 1¾ hours.

(2)

The beads were filtered and washed with Tris/0.1% Tween 20 (0.05M, pH 8, 2 ml) three times and 2 ml Tris/Tween 20 was added to the beads rotated at Ambient temperature for 1.5 hours to remove the non-specific bound catalase. The beads were washed with 0.05M phosphate buffer (pH 7, 2 ml) three times and filtered.

(3)

8.8 mg beads were added to 3.52 ml phosphate buffer (0.05M, pH 7) and 100 ul this solution was added to the hydrogen peroxide substrate solution (30% hydrogen peroxide solution diluted by 0.05M, pH 7 phosphate buffer until $A_{240nm}$ about 5.3). 15 ml of beads suspension was stirred at ambient temperature and 1.5 ml aliquots were withdrawn and checked for decreasing $A_{240nm}$ at various time intervals.

(4)

Calculate the activity unit by the following formula:
Activity unit=$(3.45/X) \times 5$ (dilution factor)
$X$ =Time (min) required for $A_{240nm}$ decreased from 0.45 to 0.40
average activity unit for the cellulose fiber was 11.4 units/mg beads
average amount of catalase bound on the fiber was 0.26 ug/mg beads

EXAMPLE 9

Coupling of Goat Anti-Mouse (GAM) IgG to 4-fluorobenzenesulfonyl chloride activated maleated cellulose rod followed by binding of horse radish peroxidase (HRPO) conjugated Mouse IgG to the gAM IgG (1)

5 mg of the 4-fluorobenzenesulfonyl chloride activated maleated cellulose rod prepared in Example 4 was incubated with 10 ul GAM IgG (10 mg/ml) and 2 ml borate buffer (0.05M, pH 9) at ambient temperature for 3 hours.

(2)

Then the sample was washed and blocked with 10% FBS (2 ml) for 1½ hours and incubated with 2 ml (4000 ng/ml) Mouse IgG-HRPO conjugate for ½ hour.

(3)

The sample was then washed with PBS/0.05% Tween 20 (20 ml), and 2 ml premixed ABTS substrate solution (solution A: solution B=1:1) was added to the sample. The sample was incubated for 20 min and the reaction was quenched with 0.25M oxalic acid solution (2 ml)

(4)

1 ml of the solution and 2 ml 0.25M oxalic acid solution were added to a cuvette and the $A_{405nm}$ was measured to obtain the concentration of the sample solution against a standardized curve of known concentrations using a spectraphotometer.

(5)

Result showed that 2.6 ng Mouse IgG conjugated HRPO was bound on 1 mg cellulose rod

EXAMPLE 10

Coupling of GAM IgG to 4-fluorobenzenesulfonyl chloride activated Sepharose beads followed by binding of HRPO conjugated Mouse IgG (1)

4-fluorobenzenesulfonyl chloride activated Sepharose beads (0.4 ml), 1.6 ml borate buffer (0.05M, pH 9) and GAM IgG (10 ul, 10 mg/ml) were incubated at ambient temperature for 1 hour.

(2)

The sample was blocked with 10% FBS (2 ml) for 1½ hours (3)

Then the sample was incubated with 2 ml (2000 ng/ml) Mouse IgG-HRPO conjugate for ½ hour.

(4)

The sample was then washed with PBS/0.05% Tween 20 (10 ml), and 2 ml premixed ABTS substrate solution (solution A: solution B=1:1) was added to 5 mg of the sample. The sample was then incubated for 20 min and the reaction quenched with 0.25M oxalic acid solution (2 ml)

(5)

The concentration of the sample solution was obtained from a standard curve of known concentrations and the result showed that 16 ng HRPO was bound per mg Sepharose beads.

The following examples compare the rate of reaction between activation of the hydroxyl groups using 4-fluorobenzenesulfonyl chloride and p-toluenesulfonyl chloride.

EXAMPLE 11

Coupling of Goat antimouse (GAM) IgG to activated magnetic polystyrene beads using 4-Fluorobenzenesulfonyl chloride or toulenesulfonyl chloride and the use of the resulting substrate for isolating a specific cell.

(1)

20 ml Borate buffer (0.05M, pH 9) was added to $12.4 \times 10^8$ 4-fluorobenzenesulfonyl chloride activated beads (uncoated polystyrene paramagnetic beads manufactured by the Pandex Division of Baxterhealthcare Corporation, Deerfield, Ill., Product Number Le3K2C), which beads were activating by a process similar to that described for Example 5, and 18.6 mg of a goat anti-mouse IgG preparation was added to the beads.

(2)

The beads were rotated at ambient temperature overnight, then washed with Dulbecco's Phosphate Buffered Saline (DPBS) and stored in a refrigerator at 4° C. Another second batch of the same quality of beads were activated by exactly the same procedure except toluenesulfonyl chloride replaced 4-fluorobenzenesulfonyl chloride in the reaction. This allowed for the following side by side comparison of the activity of each sulfonyl chloride in their ability deplete a certain cell population.

Cell Depletion (1)

Aliquots containing $2 \times 10^7$ of both bead samples were pipetted into $12 \times 75$ mm glass test tubes and washed 2 times with 2 ml DPBS, using a magnet for collection of the beads.

(2)

The amount of GAM IgG non-specific bound to the beads was reduced by incubating the beads with 0.5 to 1.0 ml DPBS containing 10% Fetal Bovine Serum (FBS) for 30 min at ambient temperature, then washing twice with 2 ml DPBS containing 2% FBS and centrifuged at high speed for one minute.

(3)

The centrifuged pellet was divided into three aliquots, with each aliquote separately incubated with one of three commercially available mouse monoclonal antibodies (the mouse antibodies recognized either the CD3, CD4 or the CD5 antigen site on human lymphocytes) for 30 min at 4° C. with occasional mixing.

(4)

Each bead samples was washed three times with 2 ml DPBS/2% FBS and the beads were resuspended in 400 ul of DPBS/2% FBS and refrigerated at 4° C. until the addition of human lymphocytes (5)

Human lymphocytes were isolated from peripheral blood using standard ficoll-hypaque separation techniques and then added at an amount of $2 \times 10^6$ cells to each bead sample in a tube raised to a final volume of 500 ul, the tubes were capped and rotated for 30 min at 4° C.

(6)

The beads with attached cells were then collected using the magnets and the supernatant transferred to $12 \times 75$ mm polypropylene test tubes. A solution of 2 ml of DPBS containing 2% FBS and 0.02% sodium azide was added to each tube and the tubes were spun at high speed for 1 min. on the centrifuge and the supernatant decanted and the tube rims blotted.

(7)

Analysis was done of the cell concentration before addition to the bead samples and then after by analyzing the supernatant from each sample using standard cytofluorograph techniques with fluorescent labeled goat antimouse antibody.

(8)

The percentages of three lymphocyte subsets before and after specific cell depletion ar shown below:

| Lymphocyte Subset | Pre-Depletion | Depletion w/ Fosyl Cl Activated Beads | Depletion w/ Tosy Cl Activated Beads |
|---|---|---|---|
| CD4 | 71.1% | 00.1% | 00.1% |
| CD5 | 85.0% | 05.5% | 10.2% |
| CD3 | 86.1% | 08.0% | 15.3% |

In each case the specific binding and biological function of the goat antimouse antibody on the beads was apparent through test and the control samples.

EXAMPLE 12

Coupling of Factor VIII to activated polystyrene paramagnetic beads (1)

The immobilization of $I^{125}$-labeled Factor VIII was compared using DYNABEADS M450 which were activated with 4-fluorobenzenesulfonyl chloride as prepared in Example 5 or activated in a similar manner using toluenesulfonyl chloride. Immobilization was assessed at a series of different Factor VIII coupling concentrations illustrated in the following table, for each Factor VIII concentration tested, 3 mg each of DYNABEAD M450 paramagnetic beads activated previously with 4-fluorobenzenesulfonyl chloride or Toluenesulfonyl chloride were resuspended in 0.05M borate buffer with 5 mM $CaCl_2$, pH 9.5 containing the desired concentration of Factor VIII.

(2)

The activated beads and Factor VIII samples were mixed for 24 hours at ambient temperature on an orbital shaker.

(3)

The beads were washed three times with 0.05% Tween-20/Phosphate Buffered Saline (4)

The Factor VIII bound to the beads was quantitated by counting the samples in a gamma counter to determine the amount of radio-label Factor VIII was bound to each bead preparation.

(5)

The number of beads remaining after the handling and washing steps was determined for each sample and the corresponding weight of the remaining beads was calculated.

(6)

The quantity of bound Factor VIII was normalized per mg of the remaining beads.

(7)

The comparative data for the two activated bead preparations is shown in tabular form below:

| Factor VIII (ug) offered per mg of beads during immobilization | Factor VIII Immobilized | |
| --- | --- | --- |
| | 4-Fluorobenzene-sulfonyl chloride activated beads | p-toluenesulfonyl chloride activated beads |
| 1 | 0.47 | 0.28 |
| 2.5 | 0.63 | 0.48 |
| 5 | 1.06 | 0.75 |
| 10 | 1.81 | 1.20 |
| 15 | 2.82 | 1.67 |
| 20 | 4.58 | 1.93 |

Another similar set of experiments was conducted comparing the two activated bead types for immobilization of Factor VIII using a 1,6-hexanediamine spacer arm. The 1,6-hexanediamine was brought into reactive contact with the beads prior to reaction with the Factor VIII to position the spacer arm between the sulfonyl group and the Factor VIII. The reactive between the 1,6-hexanediamine was performed via a reduced Schiff's base.

(1)

The previously activated 4-fluorobenzenesulfonyl chloride and Tosyl chloride beads were resuspended in a solution of 0.25M 1,6-hexanediamine in 0.05M borate buffer, pH 10.0.

(2)

The bead suspension was rotated end-over-end for 18 hours at ambient temperature.

(3)

Carbohydrate residues on $^{125}I$-labeled Factor VIII were oxidized to aldehyde moieties upon exposure to $NaIO_4$ for 60 minutes.

(4)

3 mg aliquots of amine spacer derivatized beads were rotated and end-over-end with varying amounts of Factor VIII (range 5–20 ug/mg beads) in 0.05M borate buffer/5 mM $CaCl_2$, pH 9.5 for 24 hours.

(5)

The beads were washed three times with 0.05% Tween-20/Phosphate Buffered Saline (6)

The Factor VIII bound to the beads was quantitated by counting the samples in a gamma counter to determine the amount of radiolabel bound to the bead preparations.

(7)

The number of beads remaining after the handling and washing steps was determined for each sample and the corresponding weight of the remaining beads was calculated.

(8)

The quantity of bound Factor VIII was normalized per mg of the remaining beads.

(9)

The comparative data for the two activated bead preparations is shown in tabular form below:

| Factor VIII (ug) offered per mg of beads during immobilization | Factor VIII Immobilized | |
| --- | --- | --- |
| | 4-Fluorobenzene-sulfonyl chloride activated beads | p-toluenesulfonyl chloride activated beads |
| 5 | 3.11 | 1.94 |
| 10 | 3.76 | 2.15 |
| 15 | 4.45 | 2.44 |
| 20 | 5.19 | 3.03 |

EXAMPLE 14

Activation of Cellulose Rods and Binding of I-125 labelled GAM Antibody.

The following example compares the rate of reaction between activation of the hydroxyl groups using 4-fluorobenzenesulfonyl chloride and 2,2,2-trifluoroethanesulfonyl chloride (tresyl chloride).

(1)

Cellulose rods were cut to about 1 cm long and 3 mg of cellulose rods were added to each of 3 glass test tubes.

(2)

To the three tubes was added 4 ml dry acetonitrile along with a quantity of reagents as follows:

| sample # | Reagents | Quantity |
|---|---|---|
| 1 | DMAP | 300 mg |
|   | pyridine | 150 ul |
| 2 | DMAP | 300 mg |
|   | pyridine | 150 ul |
|   | 4-fluorobenzene sulfonyl chloride | 500 mg |
| 3 | DMAP | 300 mg |
|   | pyridine | 150 ul |
|   | tresyl chloride | 450 mg |

(3)

The samples were incubated at room temperature for 6 hours and then washed with 0.05M Borate buffer(pH 9.5, 2 ml) two times, acetonitrile (2 ml) three times and borate buffer (2 ml) three times.

(4)

The samples were resuspended in 0.05M Borate buffer (pH 9.5, 3 ml) and 90 ul of a 1 mg/ml solution of $^{125}$I-GAM was added to each sample and incubated at room temperature overnight.

(5)

Samples were then counted in the scintillation counter for total counts to determine the quantity of antibody bound in each sample (6)

Each sample was washed three times with 0.05% tween/PBS and then resuspended in one ml 0.05%/PBS solution and transferred to new tubes.

(7)

Tubes used for the original incubation were washed with 0.5 ml buffer and the wash added to the new tubes. The tubes were then counted for radio-activity of each sample by a gamma counter.

| Sample Number | ug $^{125}$I-GAM offered | ug $^{125}$I-GAM bound mg rod |
|---|---|---|
| 1 | 30 | 0.48 |
| 2 | 30 | 0.94 |
| 3 | 30 | 0.87 |

While the preferred embodiments have been described, various modifications and substitutions may be made thereto without departing from the scope of the invention. Accordingly, it is to be understood that the invention has been described by way of illustration and not limitation.

What is claimed is:

1. A method for binding biologically active organic ligand to a polymeric carrier having at least one hydroxyl group, comprising the steps of
   (a) first contacting said carrier with 4-fluorobenzenesulfonyl chloride to form an activated carrier,
   (b) next contacting said activated carrier with said ligand, and then
   (c) binding said ligand to said activated carrier.

2. A method of isolating a biologically active material from a heterogeneous solution, comprising the steps of
   (a) providing a polymeric carrier having at least one hydroxyl group,
   (b) contacting said carrier with 4-fluorobenzenesulfonyl chloride to form an activated carrier,
   (c) contacting said activated carrier with a biologically active organic ligand having an affinity for said biologically active material,
   (d) binding said ligand to said activated carrier to form an affinity substrate,
   (e) contacting said affinity substrate with said heterogeneous solution,
   (f) binding said biologically active material to said affinity substrate, and
   (g) isolating said biologically active material.

3. The method of claim 1 or 2 wherein said organic ligand is a protein.

4. The method of claim 1 or 2 wherein the polymeric carrier is formed from a polystyrene or a polysaccharide.

5. The method of claim 1 or 2 wherein said polymeric carrier is selected from the group consisting of polymeric beads, polymeric fibers and polymeric rods and polymeric columns.

6. The method of claim 3 wherein said protein is an antibody.

7. The method of claim 3 wherein said protein is an antigen.

8. The method of claim 3 wherein sad protein is an enzyme.

9. The method of claim 4 wherein said polymeric carrier is formed from a polysaccharide selected from the group consisting of cross-linked agarose, cellulose, and sepharose.

10. The method of claim 5 wherein said polymeric carrier is a polymeric bead which is paramagnetic.

11. The method of claim 2 wherein said biologically active material comprises cells.

12. The method of claim 11 wherein said cells have a predetermined cell differentiation antigen.

13. The method of claim 12 wherein said cell differentiation antigen is selected from the group consisting of CD3, CD4, and CD5.

* * * * *